US009533934B2

(12) United States Patent
DeCampo et al.

(10) Patent No.: US 9,533,934 B2
(45) Date of Patent: Jan. 3, 2017

(54) HYDROLYSIS OF AN ESTER COMPOUND

(71) Applicants: RHODIA OPERATIONS, Paris (FR);
Centre National De La Recherche Scientifique, Paris (FR); Ecole Normale Superieure De Lyon, Lyons (FR)

(72) Inventors: Floryan DeCampo, Shanghai (CN);
Wenjuan Zhou, Shanghai (CN);
Zhaoyu Fan, Shanghai (CN);
Xiaoshuang Feng, Shanghai (CN);
Jean-Marc Clacens, Shanghai (CN);
Laurent Bonneviot, Lyons (FR);
Guillaume Malcouronne, Shanghai (CN)

(73) Assignees: RHODIA OPERATIONS, Paris (FR);
CENTRE NATIONAL DE LA RECHERCHE SCIENTIFIQUE, Paris (FR); ECOLE NORMALE SUPERIEURE DE LYON, Lyons (FR)

( * ) Notice: Subject to any disclaimer, the term of this patent is extended or adjusted under 35 U.S.C. 154(b) by 0 days.

(21) Appl. No.: 14/783,162

(22) PCT Filed: Apr. 11, 2014

(86) PCT No.: PCT/CN2014/075170
§ 371 (c)(1),
(2) Date: Oct. 8, 2015

(87) PCT Pub. No.: WO2014/166421
PCT Pub. Date: Oct. 16, 2014

(65) Prior Publication Data
US 2016/0297734 A1    Oct. 13, 2016

(30) Foreign Application Priority Data
Apr. 12, 2013   (WO) ................ PCT/CN2013/074168

(51) Int. Cl.
*C07C 51/09*    (2006.01)
*C07C 29/09*    (2006.01)
*B01J 31/02*    (2006.01)
*B01J 35/02*    (2006.01)
*C07C 67/08*    (2006.01)

(52) U.S. Cl.
CPC .......... *C07C 51/09* (2013.01); *B01J 31/0275* (2013.01); *B01J 35/026* (2013.01); *C07C 29/095* (2013.01); *C07C 67/08* (2013.01); *B01J 2231/005* (2013.01); *B01J 2531/002* (2013.01)

(58) Field of Classification Search
CPC .......... C07C 67/08; C07C 51/09; C07C 29/95; C07C 53/126; C07C 31/225; B01J 29/03; B01J 29/0308; B01J 35/0013; B01J 35/002
See application file for complete search history.

(56) References Cited

U.S. PATENT DOCUMENTS

| 4,185,027 A * | 1/1980 | Logan ................ C07C 51/09 554/160 |
| 5,872,289 A * | 2/1999 | Appleby ............ C07C 29/095 562/493 |
| 7,355,071 B2 | 4/2008 | Kitayama et al. |
| 2005/0240056 A1 | 10/2005 | Kitayama et al. |

FOREIGN PATENT DOCUMENTS

EP       1 591 435 A2    11/2005

OTHER PUBLICATIONS

Aveyard, R., et al., Emulsions stabilised solely by colloidal particles, 2003, Advances in Colloid and Interface Science, vol. 100-202, pp. 503-546.*
Binks, B. P. et al.: "Effects of oil type and aqueous phase composition on oil-water mixtures containing particles of intermediate hydrophobicity", Phys. Chem. Chem. Phys., vol. 2, Jun. 12, 2000, pp. 2959-2967.
Crossley, Steven et al.: "Solid Nanoparticles that Catalyze Biofuel Upgrade Reactions at the Water/Oil Interface", Science, vol. 327, Jan. 1, 2010, pp. 68-72.
Faria, Jimmy et al: "Phase-Selective Catalysis in Emulsions Stabilized by Janus Silica-Nanoparticles", Adv. Synth. Catal., Wiley-VCH Verlag GmbH & Co., KgaA, Weinheim, vol. 352, Jun. 21, 2010, pp. 2359-2364.
Horner, J. L. et al: "Emulsion Reactions: the Hydrolysis of Wool Wax", Nature Publishing Group, No. 4202, May 13, 1950, p. 771.
Jacobson, Gunilla B. et al.: "Enhanced Catalyst Reactivity and Separations Using Water/Carbon Dioxide Emulsions", American Chemical Society, vol. 121, published on Web Dec. 7, 1999, pp. 11902-11903.
Pickering, Spencer Umfreville: "CXCVI.-Emulsions", Journal of the Chemical Society, vol. 91, Jan. 1, 1907, pp. 2001-2021.
Tan, Hongyi et al: "Multifunctional amphiphilic carbonaceous microcapsules catalyze water/oil biphasic reactions", The Royal Society of Chemistry, Chem. Commun., vol. 47, Sep. 27, 2011, pp. 11903-11905.
Yang, Xiaomin et al.: "Aerobic oxidation of alcohols over carbon nanotube-supported Ru catalysts assembled at the interfaces of emulsion droplets", Applied Catalysis A: General, Elservier B.V., vol. 382, Apr. 26, 2010, pp. 131-137.
Zapata, Paula A. et al.: "Condensation/Hydrogenation of Biomass-Derived Oxygenates in Water/Oil Emulsions Stabilized by Nanohybrid Catalysts", Springer Science + Business Media, vol. 55, published online Feb. 22, 2012, pp. 38-52.
Sadaba, I. et al.: "Silica-poly(styrenesulphonic acid) nanocomposites for the catalytic dehydration of xylose to furfural", Science Direct, Applied Catalysis B: Environmental, vols. 150-151, Dec. 22, 2013, pp. 421-431.
Bingsen, Yu et al.: "Discussion of the Reaction Mechanisms of Acid Esterification and Ester Hydrolysis", Science Academic Journal Electronic Publishing House, online http://www.cnki.net, 1981.

* cited by examiner

Primary Examiner — Yate K Cutliff

(57) ABSTRACT

The present invention concerns a process to carry out an ester hydrolysis wherein the ester compound (c) is made from at least an alcohol (a) and a carboxylic acid (b), and wherein said alcohol (a) and said carboxylic acid (b) are forming a biphasic liquid system when mixed together; comprising at least a step of producing an ester compound (c)/water emulsion by using as stabilizing species amphiphilic solid particles of nanometric dimension and optionally a catalyst X.

19 Claims, No Drawings

HYDROLYSIS OF AN ESTER COMPOUND

This application is a U.S. national phase entry under 35 U.S.C. §371 of International Application No. PCT/CN2014/075170, filed on Apr. 11, 2014, which claims priority to International Application No. PCT/CN2013/074168, filed on Apr. 12, 2013. The entire contents of these applications are incorporated herein by this reference.

The present invention concerns a process to carry out an ester hydrolysis wherein the ester compound (c) is made from at least an alcohol (a) and a carboxylic acid (b), and wherein said alcohol (a) and said carboxylic acid (b) are forming a biphasic liquid system when mixed together; comprising at least a step of producing an ester compound (c)/water emulsion by using as stabilizing species amphiphilic solid particles of nanometric dimension and optionally a catalyst X.

PRIOR ART

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

Very often chemical reactions involve reactants that are not miscible such as with two incompatible phases, a hydrophobic phase and a hydrophilic phase. To solve this miscibility issue, a co-solvent can be used. However, after the synthesis this solvent must be removed.

A way to help the reactant meet without any solvent, is to emulsify the two reactants in order to create more reacting interface. However strong stirring and heating sometimes do not create enough reactive interface. A way to help stabilize the emulsion is to use an emulsifier, but even if the quantity involved is quite low compared to the reactants the separation issue is still present after the synthesis and there is then a need of a further chemical step.

In the special case of surfactant synthesis the product itself can be used as emulsifier. However the quantity needed to homogenize the mixture is not negligible and acts against the yield and the productivity.

If emulsions are not very privileged, there are several examples, including industrial processes, where syntheses are performed in these particular conditions such as with emulsion polymerization to prepare polymers. In 1950 Horner and Truter published in Nature (Nature 165, 771) that wool wax hydrolysis kinetics is improved when the reaction is performed in an emulsion. Jacobson et al. report Enhanced Catalyst Reactivity and Separations Using Water/Carbon Dioxide Emulsions stabilized by surfactants in 1999 (J. Am. Chem. Soc. 1999, 121, 11902-11903)

Emulsion stabilized by particles are reported since early 20th century, it is also known as Pickering emulsion known since Pickering, S. U. 1907, J. Chem. Soc. 91 Pages 2001-2021. Aveyard et al. published good a review in Advances in Colloid and Interface Science 100-102 (2003) 503-546. Most of academic on pickering emulsions are conducted on water/oil systems.

Binks et al. (Phys. Chem. Chem. Phys., 2000, 2, 2959-2967) studied the effect of non aqueous phase type solvent on toluene/solvent pickering emulsions. It is one of the rare paper mentioning non aqueous polar system. Authors have prepared emulsions of toluene with different other liquids including formamide, glycerol and ethylene glycol, however emulsion could not be obtained with the last two liquids, in particular glycerol.

Yang et al. (Applied Catalysis A: General 382 (2010) 131-137) demonstrate that in presence of water, it is possible to do selective aerobic oxidation of alcohol with solid catalyst at the alcohol/water interface. Resasco et al. (Science Vol 327 2010, 68-72 and Adv. Synth. Catal. 2010, 352, 2359-2364, Top. Catal. 55 (2012) 38-52) mention about "Solid Nanoparticles that Catalyze Reactions at the specific Water/Oil Interface". The reaction of their focus is a phase transfer reaction where the reactants are in the water droplet and the product of the reaction is transferred to the oil phase allowing thus to increase the conversion.

Zhou et al. (Chem. Commun. 47 (2011) 11903-11905) reported the self-assembly of amphiphilic porous hollow carbonaceous spheres (PHCSs) into pickering emulsion in water/oil biphasic phases. These particles exhibit reversible pH-dependent phase transfer behavior. Both the bare PHCSs and PHCSs functionalized with metals and agents are efficient catalysts for water/oil biphasic reactions, facilitating the recycling of catalysts and separation of products.

There is a need then to develop a new process permitting to carrying out a reaction involving a medium with a hydrophobic phase and a hydrophilic phase, without the presence of co-solvent or surfactants.

INVENTION

It appears that it is now possible to hydrolyse an ester compound made of a carboxylic acid and an alcohol that are usually forming a biphasic liquid system when mixed together; by using amphiphilic solid particles of nanometric dimension, notably comprising at the surface both hydrophilic and hydrophobic functions. Such a synthesis reaction may be made without the presence of co-solvent or surfactant.

The process of the present invention notably permits to carry out the reaction while increasing the reaction yield and/or the reaction selectivity, notably by controlling some parameters, such as the size of the droplets for example. Originality of the present invention solves the issues for esters which are generally immiscible with water, thermally instable and providing a low reactivity, as for example esters from the biomass, such as the esterolysis of triglycerides. Moreover, such amphiphilic solid particles can be removed easily after the synthesis, notably by centrifugation, by flocculation of filtration without engaging complex separation of co-solvent or surfactants. Said solid particles can be easily separated furthermore from the liquid system and reused.

The present invention then concerns a process to carry out an ester hydrolysis of an ester compound (c) made from at least an alcohol (a) and a carboxylic acid (b), and wherein said alcohol (a) and said carboxylic acid (b) are forming a biphasic liquid system when mixed together; comprising at least the following steps:
a) Producing an ester compound (c)/water emulsion by using as stabilizing species amphiphilic solid particles of nanometric dimension and optionally a catalyst X;
b) Proceeding to the reaction to hydrolyze the ester compound (c), by setting temperature, and
c) Isolating the resulting compounds.

Other characteristics, details and advantages of the invention will emerge even more fully upon reading the description which follows.

DEFINITIONS

Throughout the description, including the claims, the term "comprising one" should be understood as being synonymous with the term "comprising at least one", unless otherwise specified, and "between" should be understood as being inclusive of the limits.

In a general way, phase separation occurs as the interfacial tension between the two liquids is high. One way to reduce this interfacial tension is to modify this interface by adsorbing an object. Most commonly used objects are surfactants molecules.

Emulsion stabilized by particles relies on the fact that once a particle is adsorbed at the interface it is often difficult to remove it. The necessary energy $\Delta E$ to remove an adsorbed particle is given by the following expression:

$$\Delta E = \pi r^2 \gamma_{he}(1 \pm \cos \theta_{he})^2$$

wherein: r is the particle radius, $\gamma_{he}$ is the interfacial tension between the two liquids and $\theta_{he}$ is the contact angle of the particle in one of the phase.

From this expression, it can be seen that the adsorption energy highly depends on the particle radius and its wettability.

A "hydrophilic" molecule or portion of a molecule is one that has a tendency to interact with or be dissolved by water and other polar substances.

A "hydrophobic" molecule or portion of a molecule is one that is repelled from a mass of water and other polar substances.

"Amphiphilic" is a term describing a chemical compound possessing both hydrophilic and hydrophobic properties. Such a compound is called amphiphilic or amphipathic.

An "emulsion" is a suspension made of a first liquid in a phase made of a second liquid with which the first liquid is not miscible with the second liquid. A discontinuous phase within a continuous phase is then obtained.

Alkyl as used herein means a straight chain or branched saturated aliphatic hydrocarbon. As used herein, unless stated otherwise, the term "alkyl" means a linear or branched alkyl group optionally substituted with one or more substituent selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkyl" as used herein include, but are not limited to, n-butyl, n-pentyl, isobutyl, isopropyl, and the like.

Aryl as used herein means a 6-carbon monocyclic or 10-carbon bicyclic aromatic ring system wherein 0, 1, 2, 3, or 4 atoms of each ring are substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl. Alkenyl as used herein means a straight chain or branched, noncyclic or cyclic, unsaturated aliphatic hydrocarbon. Alkoxy as used herein is O-alkyl, wherein alkyl is as defined above.

Biphasic Liquid System

As previously defined, alcohol (a) and carboxylic acid (b) are forming a biphasic liquid system when mixed together. The ester compound and the water are also forming a biphasic liquid system when mixed together. A person skilled in the art is then perfectly able to define the couple of alcohol (a) and carboxylic acid (b) used in the present invention.

It is perfectly possible to evaluate the immiscibility of alcohol (a) and carboxylic acid (b) according to the following protocol P: 50% vol of alcohol (a) and 50% vol of carboxylic acid (b) are blended together and set a temperature T of 5° C. above the highest melting point of alcohol (a) or carboxylic acid (b), and under atmospheric pressure. The blend is stirred for 5 mins and 30 mins settling. As example of temperature T to be used in the present protocol P, when glycerol (melting point of 18° C.) and lauric acid (melting point of 43.2° C.) are used, then the test temperature T is 48.2° C. Immiscibility of alcohol (a) and carboxylic acid (b) is then asserted is a biphasic liquid system is observed.

In the same way, it is perfectly possible to evaluate the immiscibility of ester and water according to the following protocol P': 50% vol of ester and 50% vol of water are blended together and set a temperature T of 5° C. above the highest melting point of ester, and under atmospheric pressure. The blend is stirred for 5 mins and 30 mins settling. As example of temperature T to be used in the present protocol P, when monolaurylgylceryl ester (melting point of 65° C.) is used, then the test temperature T is 70° C. Immiscibility of ester compound (c) and water is then asserted is a biphasic liquid system is observed.

Alcohols (a)

Alcohols (a) may be any kinds of aliphatic or aryl alcohol providing at least one hydroxyl function. These alcohols may be primary or secondary alcohols.

Alcohol (a) may notably be a hydrophilic alcohol.

A hydrophilic alcohol (a) according to the present invention is preferably an alcohol with a value P<1 according to the following expression:

$$P = [\text{alcohol } (a)]\text{octanol}/[\text{alcohol } (a)]\text{unionized water}$$

A stock solution of the compound is prepared in either water pre-saturated with n-octanol or n-octanol pre-saturated with water. The concentration of this stock solution is known precisely before it is employed in the determination of the partition coefficient. In a separation flask, to a given volume of this solution is added the exact same volume of the other solvent (respectively n-octanol pre-satured with water or water pre-saturated with n-octanol). After addition, the flask is hand shaken for 30 seconds. After separation of the two phases, the compound concentration is determined in each phase. This may be done by taking an aliquot of each of the two phases and analyzing them by the chosen procedure. The total quantity of substance present in both phases should be calculated and compared with the quantity of the substance originally introduced. The partition coefficient P is then calculated following the above equation.

Hydrophilic alcohol (a) of the present invention may notably be a compound of formula (I) as follows:

$$R^1(OH)_p \quad \quad (I)$$

wherein $R^1$ represents the skeleton moiety of the alcohol, p is an integer ranging from 1 to 20.

$R^1$ may represent an alkyl, aryl, alkenyl or alkoxy radical, notably comprising 1 to 3000 carbon atoms. Radical $R^1$ may comprise one or several heteroatom(s) such as O or N. More, preferably $R^1$ represents the skeleton moiety of a glycerol with p is 3.

In a first embodiment, hydrophilic alcohol (a) may notably be a (poly)glycerol, defined as an oligomeric and/or polymeric chain composed of monomeric glycerol (i.e., HOCH$_2$CH(OH)CH$_2$OH) bonded together by ester linkages at the hydroxyl residue.

Specific examples of the alcohol (a) preferably having 2 to 6 hydroxyl groups may include ethylene glycol, diethylene glycol, polyethylene glycol, propylene glycol, dipropylene glycol, polypropylene glycol, 1,4-butylene glycol, 1,6-hexylene glycol, 1,8-octylene glycol, 1,10-decylene glycol, neopentyl glycol, trimethylol ethane, trimethylol propane, glycerol, diglycerol, pentaerythritol and sorbitol. These polyols may be used alone or in the form of a mixture of any optional two or more thereof. Among these polyols, from the viewpoint of a good applicability of the resultant polyglyceryl ether derivatives, preferred are glycerol, polyglycerol or mixtures thereof. The most preferred polyglycerols useful in the present invention have 2 to 30, preferably 2-20, more preferably 2-10, and most preferably 3-4 glycerol units.

In an other embodiment, alcohol (a) according to the present invention may notably be a polysaccharide, notably having the general formula C$_x$(H$_2$O)$_y$, where x is usually a number between 200 and 2500.

Alcohol (a) may notably be a hydrophobic alcohol.

A hydrophobic alcohol (a) according to the present invention is preferably an alcohol with a value P>1 according to the following expression as previously defined.

Hydrophobic alcohol may be a hydrophobic fatty alcohols that can be defined with the formula (II) as follows:

$$R^2(OH) \qquad (II)$$

wherein R$^2$ represents an alkyl, aryl, alkenyl or alkoxy radical comprising 6 to 36 carbon atoms. Radical R$^2$ may comprise one or several heteroatom(s) such as O or N.

Specific examples of the hydrophobic alcohols include 2-ethylhexyl alcohol, octyl alcohol, decyl alcohol, lauryl alcohol (dodecanol), myristyl alcohol, palmityl alcohol, stearyl alcohol, isostearyl alcohol, oleyl alcohol, ethylene glycol monomethyl ether, ethylene glycol monoethyl ether, ethylene glycol monopropyl ether, ethylene glycol monobutyl ether, propylene glycol monomethyl ether, propylene glycol monoethyl ether, propylene glycol monopropyl ether, propylene glycol monobutyl ether, polyethylene glycol monomethyl ether, polyethylene glycol monoethyl ether, polyethylene glycol monopropyl ether, polyethylene glycol monobutyl ether, polypropylene glycol monomethyl ether, polypropylene glycol monoethyl ether, polypropylene glycol monopropyl ether and polypropylene glycol monobutyl ether.

These hydrophobic alcohols may be used alone or in the form of a mixture of any optional two or more thereof. Among these hydrophobic alcohols, from the viewpoint of a good applicability of the resultant polyglyceryl ether derivatives, especially preferred are lauryl alcohol, 2-ethylhexyl alcohol and isostearyl alcohol.

Carboxylic Acid (b)

Carboxylic acid (b) may be any kinds of aliphatic or aryl carboxylic acid providing at least one carboxylic acid function.

Carboxylic acid (b) of the present invention may notably be a compound of formula (III) as follows:

$$R^3—COOH \qquad (III)$$

wherein R$^3$ represents the skeleton moiety of the carboxylic acid.

R$^3$ may represent an alkyl, aryl, alkenyl or alkoxy radical, notably comprising 1 to 3000 carbon atoms. Radical R$^3$ may comprise one or several heteroatom(s) such as O or N.

R$^3$ may notably be an alkyl radical comprising from 1 to 30 carbon atoms.

Carboxylic acids (b) of the present invention may be chosen from saturated alkyl carboxylic acids, unsaturated alkyl carboxylic acids or aryl carboxylic acid, notably be chosen in the group consisting of: myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, ricinolic acid (ricinoleic acid), tallow acid, coco acid, benzoic acid, substituted benzoic acid, citric acid, malic acid, oxalic acid etc.

Ester Compounds (c)

Ester compounds (c) according to the present invention are a class of organic compounds that contain at least an ester group, meaning a carbonyl adjacent to an ester linkage. A lot of ester compounds may be used according to the present invention. Esters of the present invention are made from at least an alcohol (a) and a carboxylic acid (b), notably made by reaction from at least an alcohol (a) and a carboxylic acid (b).

Ester compounds (c) of the present invention may be for example compounds of formula (IV) and/or (V) as follows:

$$(R^3—CO—O)p—R^1 \qquad (IV)$$

$$R^3—CO—O—R^2 \qquad (V)$$

Wherein R$^1$, R$^2$, R$^3$ and p are previously defined.

Esters of the present invention may be chosen from carboxylate esters or carbonate esters, notably be chosen from bio-based carboxylate esters or carbonate esters. Esters of the present invention may be chosen in the group consisting of: monoglyceride, diglyceride and triglyceride. More specifically, esters may be chosen in the group consisting of: monolaurylglyceryl ester, monomyristylglyceryl ester, dilaurylglyceryl ester, triformin, triacetin, triheptanoin, trimyristin, tripalmitin, trilinolein, triolein, trilaurin, and tricaprin.

Ester hydrolysis reaction of the present invention may notably be for example:

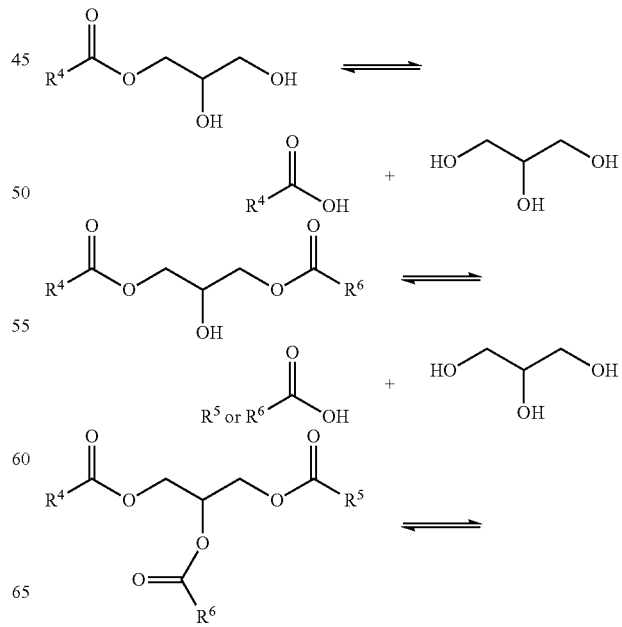

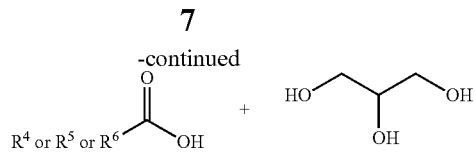

Wherein $R^4$, $R^5$ and/or $R^6$ are alkyl groups comprising from $C_4$ to $C_{36}$ carbon atoms.

In a general way, the molar ratio of alcohol (a) to carboxylic acid (b) is preferably from 1:10 to 5:1, more preferably from 1:5 to 3:1. More specifically, the molar ratio of hydrophilic alcohol (a) to hydrophobic carboxylic acid (b) is preferably from 1:5 to 3:1, more preferably from 1:3 to 1.5:1.

Catalysts

Any catalysts able to afford hydrolysis of ester compounds made of alcohol (a) and carboxylic acid (b) may be used in the process of the present invention. Examples of catalysts used in the present invention are acid or base catalysts, homogeneous or heterogeneous catalysts; such as for example Brømisted acids, vitriolic acids, nitric acids, muriatic acids, sulfonic acids, phosphoric acids, carboxylic acids and Lewis acid.

Sulfonic acid catalysts for example are preferably chosen in the group consisting of:
  perhalogenated sulfonic acids, such as triflic acid (TFA);
  benzyl derivatives sulfonic acids, such as benzyl sulfonic acid (BSA), p-toluenesulfonic acid (PTSA), and dodecyl benzyl sulfonic acid (DBSA);
  alkyl sulfonic acids, such as propyl sulfonic acid;
  cycloalkyl sulfonic acid, such as 10-camphorsulfonic acid (CSA); and
  alkoxyglyceryl sulfonic acids, such as lauryl glyceryl sulfonic acid.

Basic catalysts are preferably chosen in the group consisting of inorganic base catalysts or organic amino catalysts, such as guanidine or pyridine.

The amount of catalyst X used in the present reaction is usually comprised between 0.01 and 100% molar, preferably between 0.5 and 50% molar, per mol of ester compound (c).

The molar ratio of catalyst X to the ester compound (c) is usually comprised between 0.0001% and 10%, preferably between 0.001% and 1%.

The molar of catalyst X to the ester compound (c) is the the percentage of catalytic acid sites compared to the total molar amount of ester compound (c).

Amphiphilic Particles

Solid particles of nanometric dimension of the instant invention are notably isotrope or anisotrope particles, having generally an average diameter comprised between 2 and 200 nm, preferably between 10 and 50 nm. This can be determined by visually examining a micrograph of a transmission electron microscopy "TEM" image, measuring the diameter of the particles in the image, and calculating the average primary particle size of the measured particles based on magnification of the TEM image. One of ordinary skill in the art will understand how to prepare such a TEM image and determine the primary particle size based on the magnification. The primary particle size of a particle refers to the smallest diameter sphere that will completely enclose the particle. As used herein, the term "primary particle size" refers to the size of an individual particle as opposed to an agglomeration of two or more individual particles.

The shape or morphology of the solid particle stabilizer can vary. For example, generally spherical morphologies can be used, as well as particles that are cubic, platy, or acicular (elongated or fibrous), such as sticks or needles.

Any solid particles that act as a stabilizer may be used in the present invention. Suitable particles include, for example, inorganic materials, such as water insoluble metal salts or metal hydroxides or metal oxides or mixed metal oxides or clays.

Specific non-limiting examples include bentonite, tin oxide, magnesium aluminum silicate, magnesium oxide, titanium oxide, barium sulphate and/or silica, such as is described in U.S. Pat. No. 4,833,060 at col. 4, lines 54-61, the cited portion of which being incorporated herein by reference, and alumina as described in U.S. application 2005/0156340.

Said particles are usually inorganics such as for example made of an oxide, hydroxide and/or oxy-hydroxyde of at least one metal chosen from cerium, aluminium, titanium or silicium. Particles of the invention may also be made of a phosphate or a hydrogenophosphate of metals or rare earths.

Particles can also be organic, obtained from reticulation of polymer chains such as latex particles, polymeric nanoparticles with core-shell structures which are composed by amphiphilic chains cross-linked at the core or on the layer of shell.

Particles of the present invention may also be a combination of inorganic particles with organic chains, such as for instance alkyl or organic polymeric chains. These particles may notably be obtained by absorption, grafting, co-precipitation, sol-gelation, hydrothermal synthesis, solvothermal synthesis, encapsulation or preparation through emulsion or micelles. As suitable organic-inorganic nanoparticles of the present invention, polystyrene-silica nanoparticles may notably be used in the ester hydrolysis process, such as described in the paper of M. Lopex Granados on Silica-poly (styrenesulphonic acid) nanocomposites for the catalytic dehydration of xylose to furfural published on applied catalysis B: Environmental 150-151(2014), 421-431.

It can be advantageous that the particles of the invention may have a colloidal behaviour, preferably with an inter particular agglomeration rate (number of agglomerated particles/total number of particles) inferior or equal to 5%, more preferably inferior or equal to 2%. In certain embodiments, the solid particles, such as silica and/or alumina particles, are introduced in the form of colloidal dispersion, wherein finely divided solid particles are dispersed within a continuous medium in a manner that prevents them from being filtered easily or settled rapidly.

Particles of the invention are amphiphilic and then comprise at their surface both hydrophilic and hydrophobic functions.

Hydrophilic nature is usually provided by the presence of hydrophilic groups. These groups may be neutral such as $-OH$, $-COON$, $-PO_3H_2$, $-SO_3H$ as example, or preferentially under their anionic or cationic corresponding forms.

Hydrophobic nature is usually provided by the presence of hydrophobic groups such as organic chains having a hydrophobic nature. Said chains are defined as organic chains having a hydrophobic character such as these chains are soluble in a hydrophobic solvent and less soluble, notably insoluble, in water. Organic chains having a hydrophobic nature may have at least 50% wt, preferentially at least 80% wt of hydrophobic groups such as alkylated groups, or alkoxylated groups.

Hydrophobic groups are preferably alkyl chains comprising 1 to 30 carbon atoms, more preferably from 1 to 8 carbon atoms or alkoxylated groups notably comprising 1 to 10 units of ethylene oxide $-CH_2CH_2O-$ groups The exact nature of the link existing between organic chains and the surface of the solid particles can vary in a large measure and may be for example a covalent bond, or physical adsorption more often including an electrostatic bond, an ionic bond and a hydrogen bond. Covalent bonds can be obtained by grafting or co-condensation or co-precipitation.

The grafting rate of the particle surface by hydrophobic groups may be comprised between 5 and 90% of the original amount of hydroxyl groups, preferably between 30 and 70%. This grafting rate may be evaluated by a thermal decomposition of the particles and then calculate the amount of water formed during the decomposition. It is then possible to proceed to an extrapolation of the number of hydroxyl group.

In a preferred embodiment of the invention, the bonds between the organic chains of hydrophobic nature and the surface of the particles are covalent bonds. In this case, these are usually made covalent bonds between atoms of metal particles and organic chains, usually via oxygen atoms initially present in a hydroxyl metal group of the particle surface.

Preferably, the metal atom of these groups hydroxylated metal surface is an atom of silicon, aluminum, or titanium. In this case, the particles are formed at least partially of silicon oxide, oxy-hydroxide of aluminum and/or titanium oxide, this or these oxide (s) and/or oxy-hydroxide being at least this (s) on the surface. Thus, the particles can then be formed such oxide (s), hydroxide (s) and/or oxy-hydroxide (s) of chemical nature variable, having a surface layer of silicon oxide oxy-aluminum hydroxide and/or titanium oxide, made for example by after-treatment surface.

The organic chains covalently linked are generally introduced by this embodiment of the invention by condensation of a silanol group SiOH on the particle, according to the general reaction:

[particle]-M-OH+HO-Si [organic chain]->[particle]-
  M-O—Si-[organic chain]

wherein M is Si, Al or Ti.

In this case, the silanol group SiOH usually comes from the acid hydrolysis, neutral, or basic group of a alkoxysilane, for example acid hydrolysis of a compound or trimethoxy-alkysilane triethoxyalkylsilane.

The amphiphilic solid particles of nanometric dimension may also be obtained by co-precipitation of compounds providing hydrophilic function and compounds providing hydrophobic function. For examples, silica nanoparticles may be obtained by co-precipitation of hydrophilic silane compounds and hydrophobic silane compounds. Pavithran et al. (Langmuir, 26 (2010) 730-735) reported bifunctionalized silica spheres carring aminopropyl and vinyl groups by hydrolytic co-condensation.

Whatever the exact nature of links implemented to ensure cohesion between the hydrophobic chains and the particle surface, it is preferred that the bonds between the chains and hydrophobic particles are inhomogeneously distributed on the surface of said particles, whereby said particles modified surface have a first area to overall hydrophilic nature and a second area to overall hydrophobic character.

Amphiphilic nature of the nanoparticles of the present invention may notably be asserted as follows. When 1% by weight of nanoparticles are mixed with 50% vol of ester and 50% vol of water at a temperature T of 5° C. above the highest melting point of ester, and under atmospheric pressure and after stirring for 5 minutes at 13000 rpm and a subsequent storage of 24 hours, an emulsion with droplets of ester/water or water/ester is observed. Amphiphilic nature of nanoparticles is then asserted if a biphasic liquid system is observed after storage.

It has to be noticed that according to the nature of hydrophilic and hydrophobic functions at the surface of particles, said particles may also act as emulsifier and also catalyst. It appears then that the stabilizing species amphiphilic solid particles of nanometric dimension used to produce the ester compound (c)/water emulsion, notably by the presence of hydrophilic and hydrophobic functions at the surface of particles, may act as catalyst for the hydrolysis reaction of the ester of compound (c).

Indeed, amphiphilic solid particles of nanometric dimension may provide a catalytic function permitting to carry out the ester hydrolysis of the ester compound (c) of the present invention. This catalytic function may be obtained by the use of groups directly grafted or supported to said particles. These groups may then act as catalyst in the reaction of the present invention. Sulfonic (—SO$_3$H) or sulfate are particularly efficient as both catalytic and hydrophilic functions for amphiphilic particles.

Nanoparticles of the present invention may notably provide sulfonic acid function containing group(s). These groups may also comprise alkyl, peralkyl or aryl group, such as for instance:

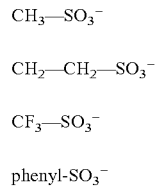

It is advantageous to choose the concentration of amphiphilic particles according to the invention to be greater than 0.1% by weight, particularly advantageously between 0.1% by weight and 30% by weight, based on the total weight of the preparations.

Process Parameters

In order to obtain the ester/water emulsion of step a), it is first necessary to obtain a blend of at least ester, water, optionally the catalyst X and amphiphilic solid particles of nanometric dimension. The particles can be added/dispersed in either phase prior to the addition of the second phase and global emulsification. Emulsification can also be carried out after introduction of all components in any order in the container vessel.

It is notably possible to produce emulsions comprising the following steps: (i) a blend of amphiphilic particles is produced in a continuous phase by addition of the particles to the liquid without stirring; and (ii) the phase to be dispersed is then added to the blend obtained in step (i) and emulsion is then obtained by stirring.

It can also be possible to produce emulsions comprising the following steps: (i) a dispersion of amphiphilic particles is produced in a continuous phase by stirring; and (ii) while stirring, the emulsion is obtained by adding the phase to be dispersed to the dispersion obtained in step (i).

The weight ratio of ester compound (c) to water at the start of the reaction is preferably comprised between 0.05:1 to 1:0.05, more preferably between 0.2:1 to 1:0.2.

Emulsification instrument can be any instrument giving high energy such as ultra sound, or high shear such as homogenizer, or other stirring methods.

Preferably, the medium used in the present process of the invention is substantially free or, in some cases, completely free of any surfactant (other than the amphiphilic particles of the invention), at the start of the reaction. As used herein, the term "surfactant" refers to materials that have an amphiphilic molecular structure, which includes a polar hydrophilic molecular moiety and a nonpolar lipophilic molecular moiety, and which acts to lower the interfacial tension between the dispersed phase and the continuous phase in an emulsion. As will be appreciated, surfactants can be classified as ionic (anionic, cationic, and amphoteric) or nonionic. As used herein, the term "substantially free" when used with reference to the absence of surfactant in the medium of the present invention, means that the emulsion comprises less than 0.1% wt of surfactant, based on the total weight of the medium, notably at the beginning of the reaction; and preferably during the reaction. As used herein, the term "completely free" when used with reference to the absence of surfactant in the medium of the present invention, means that the emulsion comprises no surfactant at all.

In step b), the reaction of hydrolysis is led by setting the appropriate temperature. Said temperature to lead the reaction is of course linked to the nature of alcohol (a) and carboxylic acid (b) and the resulting ester compound (c). The reaction temperature used in step b) to proceed with the reaction is generally comprised between 50° C. and 250° C., preferably between 80° C. and 150° C.

Several stirring methods may be used during the reaction; preferably a continuous stirring is maintained in step b). During this step, the reaction may be carried out under atmospheric pressure or under pressure. Said reaction can be made under inert gas or air for example.

Several known methods of purification of the resulting compounds at the end of the reaction, notably at least alcohol (a) and carboxylic acid (b) may be used, such as for example extraction, distillation, and/or crystallisation.

Illustrating the invention are the following examples that are not to be considered as limiting the invention to their details.

EXPERIMENTAL PART

Example 1

Propyl and Sulfonic Acid-Grafted Silica Nanoparticles 1.1 Grafting of Propyl and Mercapto Functions Aerosil 200 (0.5 g) from Evonik Degussa was placed in a round flask, and then cyclohexane (50 mL) was added. The mixture was stirred until homogenous distribution of Aerosil 200. Then, different amount of silanes [20%: 0.4 mL of (OMe)$_3$Si(CH$_2$)$_3$SH and 1.5 mL of (OMe)$_3$Si(CH$_2$)$_3$] were added and stirred in flask, respectively. Then, 4-toluene sulfonic acid (0.0033 g) was added. The flask was placed on a pre-heated hotplate at 120° C. and the mixture was stirred for 4 hours. After cooling down to room temperature, the mixture was filtrated or centrifuged and washed by cyclohexane and ethanol for several times in order to remove 4-toluene sulfonic acid and unreacted silanes. The obtained samples were heated at 100° C. overnight.

1.2 H$_2$O$_2$ Oxidation

The above samples were placed in a round flask. H$_2$O$_2$ (30 wt %, m(H$_2$O$_2$): m(sample)=60:1) was added into flask and the mixtures were stirred at 40° C. for 24 h. After filtration and washing by Ethanol at 95%, the samples were dried at 40° C. under vacuum for 4 h.

1.3 Acidification

Samples and H$_2$SO$_4$ solution (0.8 M, m (H$_2$SO$_4$): m(sample)=60:1) were added in a flask. The mixtures were stirred at room temperature for 2 h. After filtration and washing by ethanol (95%) until suspension pH equal to 7, the obtained solids were dried at 100° C.

Example 2

Co-Precipitated Silica Nanoparticles Functionalized by Octadecyl and Sulfonic Acid Groups A solution of ammonium hydroxide (NH$_3$—H$_2$O) (16.2 ml, 25-28%) in absolute ethanol (200 ml) and bi-distilled water (28 ml) was firstly prepared in 40° C. for 10 minutes. A solution of TEOS (9.3 g) in ethanol (9.3 g) was added dropwise with vigorous stirring in the first solution. After about 5 minutes of pre-hydrolysis of TEOS, octadecyl silane ((OMe)$_3$Si(CH$_2$)$_{17}$CH$_3$) and SH-siliane were added in succession with a delay of 5 minutes. The TEOS/organosilanes molar ratio is 80/20, with C$_{18}$ silane/SH silane molar ratio of 4. After 30 minutes, the white precipitation was separated by centrifugation at 8,000 rpm for 15 minutes. The obtained solids were washed with and centrifuged several times until that the suspended solution was neutral. The oxidation of —SH to —SO$_3$H in samples was oxidized by H$_2$O$_2$ in the same condition as the above method. Finally, samples were treated by acid wash same as above described.

Example 3

Esterolysis of Monolaurylglyceryl Ester by Several Catalysts

Reaction:

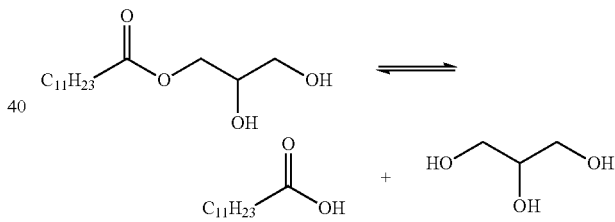

Silica nanoparticles bearing alkyls and alkyl sulfonic aid have been used to catalyse the hydrolysis reaction of monolaurylglyceryl ester. Conversions and reaction conditions were listed in Table 1.

TABLE 1

| Catalyst | Catalyst (weight %) | Catalyst (molar %) | Ester/H$_2$O (weight) | Temp/Time | Conversion | TON |
|---|---|---|---|---|---|---|
| TFA | 1.1% | 2% | 2:1 | 70° C./5 h | 36.1% | 17 |
| SA | 0.73% | 2% | 2:1 | 100° C./5 h | 37.1% | 18 |
| PTSA | 1% | 16.9% | 1:3 | 95° C./11 h | 52.9% | 32 |
| SiO$_2$ 20/80 SO$_3$H/C$_3$ | 2% | 0.0116% | 1:3 | 95° C./11 h | 6% | 496 |
| SiO$_2$ 20/80 SO$_3$H/C$_3$ | 10% | 0.0519% | 1:3 | 95° C./11 h | 48.7% | 886 |
| SiO$_2$ 20/80 SO$_3$H/C18 | 4% | 0.0151% | 1:3 | 95° C./11 h | 22.5% | 1403 |
| SiO$_2$ 20/80 SH/C$_3$ | 2% particles | 0% | 1:3 | 95° C./11 h | 0.6% | NA |
| PTSA + SiO$_2$ 20/80 SH/C$_3$ | 1%, 2% | 16.9% | 1:3 | 95° C./11 h | 57.1% | 32 |

TABLE 1-continued

| Catalyst | Catalyst (weight %) | Catalyst (molar %) | Ester/ H$_2$O (weight) | Temp/ Time | Conversion | TON |
|---|---|---|---|---|---|---|
| NH$_4$Cl + SiO$_2$ 20/80 SH/C$_3$ | 1%, 2% | 0% | 1:3 | 95° C./11 h | 2.3% | NA |

TFA is CF$_3$SO$_3$H. SA is H$_2$SO$_4$. PTSA is CH$_3$C$_6$H$_4$SO$_3$H

Catalyst (weight %) corresponds to the weight amount of catalyst to the weight amount of ester. Catalyst (molar %) corresponds to the molar amount of catalyst acid sites to the molar amount of ester. The ester/H$_2$O ratio corresponds to the weight amount of ester to the weight amount of water. TON is the turn over number corresponding to the ratio between the molar amount of monolaurin ester by molar amount of acid functions.

It appears then that the catalytic activity of grafted silica particles is 100 to 1000 times better than PTSA, CF$_3$SO$_3$H or H$_2$SO$_4$ based on conversion of MGLE per molar acid. The maximum conversion of MGLE by 10% particles added can reach 48% at 10 hours.

When 2% SiO$_2$ 20/80 SH/C$_3$ are added as catalyst in the reaction system, the wettability of these particles are almost same with SiO$_2$ 20/80 SO$_3$H/C$_3$; but the conversion of MLGE is only 0.6%. This means that particles without catalytic functional group can't help the esterolysis.

When 1% PTSA with 2% SiO$_2$ 20/80 SH/C$_3$, are used as catalysts, the conversion increased+8% compared with 1% obtained with PTSA itself. This result reveals that particles have helped to increase the interface between the two phases and that it leads to a higher conversion of the reaction.

The last reaction was done with 1% NH$_4$Cl and 2% SiO$_2$ 20/80 SH/C$_3$ as catalyst. The pH value of 1% NH$_4$Cl is much lower than 1% acid like PTSA, CF$_3$SO$_3$H, or H$_2$SO$_4$. Generally, the esterolysis reaction won't happen under such conditions; but silica nanoparticles of the present invention helped it to get conversion at 2.3%.

NMR spectrum of MLGE:

$^1$H NMR (300 MHz, DMSO-d$_6$): $\delta_H$=4.89 (d, J=5.1 Hz, 1H), 4.64 (t, J=5.7 Hz, 1H), 4.02 (2dd, J=14.8, 4.2 Hz, 1H), 3.88 (2dd, J=14.8, 6.6 Hz, 1H), 3.65-3.59 (m, 1H), 3.68-3.31 (m, 3H), 2.28 (t, J=7.5 Hz, 21H), 1.53-1.49 (m, 2H), 1.24 (br s, 16H), 0.85 (t, J=6.3 Hz, 3H) ppm NMR spectrum of lauric acid $^1$H NMR (300 MHz, DMSO-d$_6$): $\delta_H$=11.97 (S, 1H), 2.17 (t, J=7.8 Hz, 2H), 1.50-1.45 (m, 2H), 1.24 (br s, 16H), 0.85 (t, J=6.9 Hz, 3H) ppm NMR Spectrum of Glycerol $^1$H NMR (300 MHz, DMSO-d$_6$): $\delta_H$=4.53 (d, J=4.8 Hz, 1H), 4.34 (t, J=5.4 Hz, 2H), 3.43-3.24 (m, 5H) ppm It appears then that NMR is a good method for the quantification of lauric acid content in the mixture. There is no overlap at 2.17-2.28 ppm (the second CH$_2$ from CO) among lauric acid, monlaurylglyceryl ester and glycerol. So the NMR quantitative method was developed based on this fact. The linearity R$^2$ is 0.999.

Example 4

Phenyl Sulfonic Acid-Grafted Silica Amphiphilic Nanoparticles

I.1. Preparation of MCM41

A solution of sodium silicate was first prepared: 32 g of NaOH were stirred with 187 ml of Ludox. This mixture is stirred 24 h at 40° C.

In a first erlen, 345 mL of this sodium silicate solution were stirred 1 hour at 60° C. In a second erlen, 13.83 g of CTATos (cetyltrimethyl amine tosylate) are stirred with 500 mL of water during 1 hour at 60° C. Then the first erlen is slowly added to the second erlen. This new mixture is stirred at 60° C. until we obtained an homogenous solution by around 1 hour. This new solution is divided in equal part in the autoclaves and put into the microwave. The ramp from room temperature to 180° C. is 15 min, the step at 180° C. is 9 min. Then the mixture is filtrated under vacuum and wash with ethanol (three times 50 mL) and acetone (one time 50 mL). Then the powder is dry overnight in oven at 80° C. and we obtain 22.61 g of white powder. TGA, BET and XRD were done.

I.2. Surfactant Extraction 22 g of MCM41 previously obtained were dispersed into 350 mL of ethanol, 2 equivalent of hydrochloric acid are added. This mixture is stirred 1 hour at 60° C., then filtrated under vacuum and wash with ethanol (three times 50 mL) and acetone (one time 50 mL). This operation was repeated twice. Then the powder is dry overnight in oven at 80° C. TGA, BET and XRD were done.

If there is still some surfactant, the rest is removed by a soft calcination under nitrogen: 5° C. per minute until 500° C., then keep this temperature during 2 hours. Then the powder is washed with ethanol (three times 50 mL) and acetone (one time 50 mL). Then the powder is dry overnight in oven at 80° C. TGA, BET and XRD were done.

I.3. Grafting of Trimethoxyphenylsilane on MCM41

5.2 g of MCM41 were first activated at 130° C. during 1 hour. After cooling down to room temperature, 150 mL of cyclohexane are added. This mixture is stirred until we get an homogeneous dispersion. Then the trimethoxyphenylsilane (1 eq-7.28 mmol-1.36 mL) is added. The mixture is stirred at reflux at 80° C. during 5 hours. Then the mixture is filtrated under vacuum and wash with ethanol (three times 50 mL) and acetone (one time 50 mL). Then the powder is dry overnight in oven at 80° C. and we obtain 22.61 g of white powder. TGA, BET and XRD were done.

I.4. Sulfonation of the Trimethoxyphenylsilane-MCM41

The silica is introduced to a glass column between 2 filters. At the bottom of the column a round flask with 50 mL of sulfuric fuming acid (35%) was fixed. The sulfuric fuming acid flows throw the silica in order to sulfonate it. Some argon bubbled in the sulfuric fuming acid in order to help him to go up to the column. At the top of the column after the filter the sulfuric fuming acid go to a trap in order to avoid sulfuric acid vapor go out. In the trap helianthine color indicator was put in order to know when the water in the trap becomes acid (which means the reaction is over). Then the powder is washed with Ethanol (three times 50 mL) and acetone (one time 50 mL). Then the powder is dry overnight in oven at 80° C. TGA, BET and XRD were done.

I.5. Amphiphilic Nature of Nanoparticles

1% by weight of nanoparticles previously obtained are mixed with 50% vol of ester and 50% vol of water at 70° C.

The resulting blend is stirred for 5 minutes at 13000 rpm. After a storage of 24 hours, the medium is observed with a microscope. Observation of an emulsion with droplets of ester/water or water/ester is an indication that nanoparticles provide an amphiphilic property.

Example 5

Esterolysis of Monolaurylglyceryl Ester by Several Catalysts

Reaction:

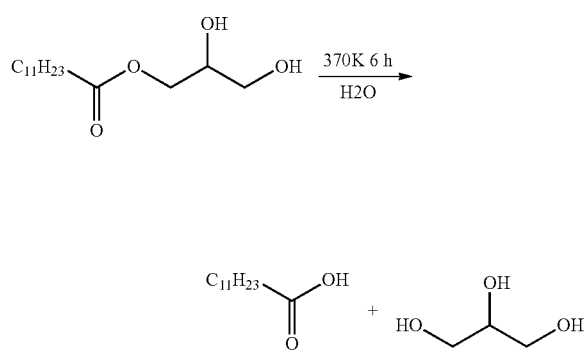

Silica nanoparticles bearing alkyls and alkyl sulfonic acid have been used to catalyse the hydrolysis reaction of monolaurylglyceryl ester. Conversions and reaction conditions were listed in Table 2.

TABLE 2

| Catalyst | Catalyst (weight %) | Catalyst (molar %) | Ester/H$_2$O (weight) | Temp/Time | Conversion | TON |
|---|---|---|---|---|---|---|
| MCM41-Phenyl-SO$_3$H | 0.2% | 0.0013 eq | 1:3 | 95° C./24 h | 31.91 | 237.87 |
| MCM41-Phenyl-SO$_3$H | 10% | 0.058 eq | 1:3 | 95° C./24 h | 47.09 | 8.17 |
| PTSA | 1% | 0.017 eq | 1:3 | 95° C./24 h | 53.7 | 31.29 |
| PTSA | 10% | 0.14 eq | 1:3 | 95° C./24 h | 81.41 | 5.8 |

Catalyst (weight %) corresponds to the weight amount of catalyst to the weight amount of ester. Catalyst (molar %) corresponds to the molar amount of catalyst acid sites to the molar amount of ester. The ester/H$_2$O ratio corresponds to the weight amount of ester to the weight amount of water. TON is the turn over number corresponding to the ratio between the molar amount of monolaurin ester by molar amount of acid functions.

It appears then that the TON is higher with silica particles of the present invention. The silica particles increased the contact of monolaurylglyceryl ester and water. Then the catalytic sites on silica surface may help the catalytic hydrolysis also.

Example 6

Esterolysis of trilaurylglyceryl ester by several catalysts

Reaction:

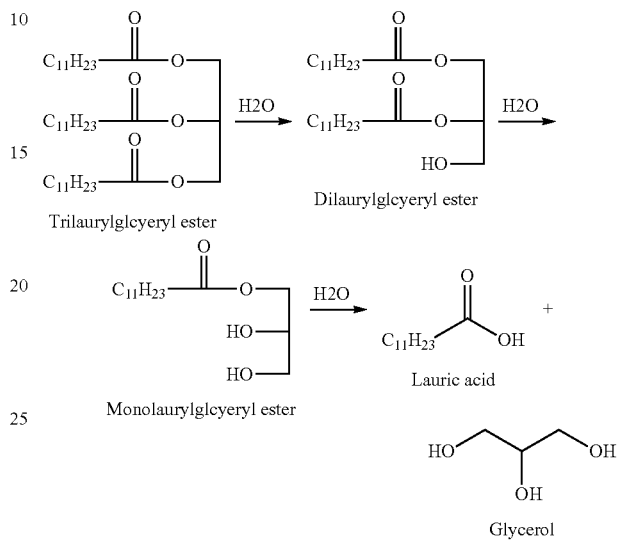

Silica nanoparticles bearing alkyls and alkyl sulfonic aid have been used with TFA to catalyse the hydrolysis reaction of trilaurylglyceryl ester. Conversions and reaction conditions were listed in Table 3.

TABLE 3

| Catalyst | Catalyst (weight %) | Catalyst (molar %) | Ester/H$_2$O (weight) | Temp/Time | Conversion | TON |
|---|---|---|---|---|---|---|
| TFA | 2.3% | 0.1 eq | 1:3 | 95° C./8 h | 26.1% | 2.6 |
| TFA | 23.3% | 1 eq | 1:3 | 95° C./8 h | 68.2% | 0.68 |
| TFA | 69.8% | 3 eq | 1:3 | 95° C./8 h | 93.2% | 0.31 |
| H$_2$SO$_4$ | 23.0% | 3 eq | 1:3 | 95° C./8 h | 72.4% | 0.24 |
| H$_2$SO$_4$ | 7.7% | 1 eq | 1:3 | 95° C./8 h | 32.9% | 0.33 |
| TFA + SiO$_2$ 20/80 SO$_3$H/C$_3$ | 23.3%, 4% | 1 eq, 0.004 eq | 1:3 | 95° C./8 h | 76.8% | 0.77 |
| TFA + SiO$_2$ 20/80 SO$_3$H/C$_8$ | 23.3%, 4% | 1 eq, 0.004 eq | 1:3 | 95° C./8 h | 87.9% | 0.88 |
| TFA + SiO$_2$ 20/80 SO$_3$H/C$_{18}$ | 23.3%, 4% | 1 eq, 0.004 eq | 1:3 | 95° C./8 h | 78.2% | 0.78 |

Catalyst (weight %) corresponds to the weight amount of catalyst to the weight amount of ester. Catalyst (molar %) corresponds to the molar amount of catalyst acid sites to the molar amount of ester. The ester/H$_2$O ratio corresponds to the weight amount of ester to the weight amount of water. TON is the turn over number corresponding to the ratio between the molar amount of trilaurin ester by molar amount of acid functions.

It appears then that the catalytic activity can be increased with silica particles of the present invention, notably by improving the contact of trilaurylglyceryl ester and water and the presence of catalytic sites on silica surface.

What is claimed is:

1. A process for carrying out an ester hydrolysis of an ester compound (c) made from at least an alcohol (a) and a carboxylic acid (b), and wherein said alcohol (a) and said carboxylic acid (b) form a biphasic liquid system when mixed together; the process comprising:
    a) Producing an ester compound (c)/water emulsion by using amphiphilic solid particles of nanometric dimension as stabilizing species and optionally a catalyst X;
    b) hydrolyzing the ester compound (c), by setting the temperature, and
    c) Isolating the resulting compounds.

2. The process according to claim 1, wherein the immiscibility of alcohol (a) and carboxylic acid (b) is defined according to protocol P, protocol P
    blending alcohol (a) and carboxylic acid (b) together,
    setting a temperature T, which is 5° C. above the highest of the melting points of alcohol (a) or carboxylic acid (b), under atmospheric pressure,
    stirring the blend for 5 mins, and
    settling for 30 mins.

3. The process according to claim 1, wherein alcohol (a) is a hydrophilic alcohol of formula (I) as follows:

$$R^1(OH)p \qquad (I)$$

wherein $R^1$ represents the skeleton moiety of the alcohol, p is an integer ranging from 1 to 20.

4. The process according to claim 3, wherein $R^1$ represents the skeleton moiety of a glycerol and p is 3.

5. The process according to anyone of claim 1, wherein alcohol (a) is selected from the group consisting of: ethylene glycol, diethylene glycol, polyethylene glycol, propylene glycol, dipropylene glycol, polypropylene glycol, 1,4-butylene glycol, 1,6-hexylene glycol, 1,8-octylene glycol, 1,10-decylene glycol, neopentyl glycol, trimethylol ethane, trimethylol propane, glycerol, diglycerol, pentaerythritol and sorbitol.

6. The process according to claim 1, wherein alcohol (a) is a hydrophobic alcohol of formula (II) as follows:

$$R^2(OH) \qquad (II)$$

wherein $R^2$ represents an alkyl, aryl, alkenyl or alkoxy radical comprising 6 to 36 carbon atoms.

7. The process according to claim 6, wherein alcohol (a) is selected from the group consisting of: 2-ethylhexyl alcohol, octyl alcohol, decyl alcohol, lauryl alcohol, myristyl alcohol, palmityl alcohol, stearyl alcohol, isostearyl alcohol, oleyl alcohol, ethylene glycol monomethyl ether, ethylene glycol monoethyl ether, ethylene glycol monopropyl ether, ethylene glycol monobutyl ether, propylene glycol monomethyl ether, propylene glycol monoethyl ether, propylene glycol monopropyl ether, propylene glycol monobutyl ether, polyethylene glycol monomethyl ether, polyethylene glycol monoethyl ether, polyethylene glycol monopropyl ether, polyethylene glycol monobutyl ether, polypropylene glycol monomethyl ether, polypropylene glycol monoethyl ether, polypropylene glycol monopropyl ether and polypropylene glycol monobutyl ether.

8. The process according to anyone of claim 1, wherein carboxylic acid (b) is a compound of formula (III) as follows:

$$R^3-COOH \qquad (III)$$

wherein $R^3$ represents the skeleton moiety of the carboxylic acid.

9. The process according to claim 8, wherein $R^3$ is an alkyl radical comprising from 1 to 30 carbon atoms.

10. The process according to anyone of claim 1, wherein carboxylic acid (b) is selected from the group consisting of: myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, ricinolic acid, tallow acid, coco acid, benzoic acid, substituted benzoic acid, citric acid, malic acid, and oxalic acid.

11. The process according to claim 1, wherein ester compound (c) is a compound of formula (IV) and/or formula (V) as follows:

$$(R^3-CO-O)p-R^1 \qquad (IV)$$

$$R^3-CO-O-R^2 \qquad (V)$$

Wherein
    $R^1$ represents the skeleton moiety of the alcohol, p is an integer ranging from 1 to 20,
    $R^2$ represents an alkyl, aryl, alkenyl or alkoxy radical comprising 6 to 36 carbon atoms, and
    $R^3$ represents the skeleton moiety of the carboxylic acid.

12. The process according to anyone of claim 1, wherein the ester compound (c) is selected from the group consisting of: monoglyceride, diglyceride and triglyceride.

13. The process according to claim 1, wherein ester compound (c) is selected from the group consisting of: monolaurylglyceryl ester, monomyristylglyceryl ester, dilaurylglyceryl ester, triformin, triacetin, triheptanoin, trimyristin, tripalmitin, trilinolein, triolein, trilaurin, and tricaprin.

14. The process according to claim 1, wherein the catalyst X is selected from the group consisting of: Brønsted acids, vitriolic acids, nitric acids, muriatic acids, sulfonic acids, phosphoric acids, carboxylic acids and Lewis acid.

15. The process according to anyone of claim 1, wherein the catalyst X is a sulfonic acid catalyst selected from the group consisting of:
    perhalogenated sulfonic acids;
    benzyl derivatives sulfonic acids;
    alkyl sulfonic acids;
    cycloalkyl sulfonic acid; and
    alkoxyglyceryl sulfonic acids.

16. The process according to claim 1, wherein the amphiphilic solid particles of nanometric dimension provide a catalytic function permitting the carrying out of the ester hydrolysis of the ester compound (c).

17. The process according to claim 16, wherein the amphiphilic solid particles of nanometric dimension comprise —$SO_3H$ groups directly grafted or supported on said particles.

18. The process according to claim 1, wherein the weight ratio of ester compound (c) to water at the start of the reaction is between 0.05:1 and 1:0.05.

19. The process according to claim 1, wherein the reaction temperature used in step b) is between 50° C. and 250° C.

* * * * *